United States Patent
Muratoglu et al.

(10) Patent No.: US 11,970,600 B2
(45) Date of Patent: Apr. 30, 2024

(54) DI-CUMYL PEROXIDE CROSSLINKING OF UHMWPE

(71) Applicant: The General Hospital Corporation, Boston, MA (US)

(72) Inventors: Orhun K. Muratoglu, Cambridge, MA (US); Ebru Oral, Newton, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

(21) Appl. No.: 17/703,288

(22) Filed: Mar. 24, 2022

(65) Prior Publication Data

US 2022/0325082 A1   Oct. 13, 2022

Related U.S. Application Data

(60) Provisional application No. 63/169,120, filed on Mar. 31, 2021.

(51) Int. Cl.
*C08L 23/06* (2006.01)
*A61L 31/04* (2006.01)
*C08J 3/24* (2006.01)

(52) U.S. Cl.
CPC ............ *C08L 23/06* (2013.01); *A61L 31/048* (2013.01); *C08J 3/24* (2013.01); *C08J 2323/06* (2013.01)

(58) Field of Classification Search
CPC ...... C08L 23/06; C08L 2207/068; C08K 5/14
See application file for complete search history.

(56) References Cited

U.S. PATENT DOCUMENTS

| | | | |
|---|---|---|---|
| 3,974,132 | A | 8/1976 | Valdiserri |
| 5,032,450 | A | 7/1991 | Rechlicz et al. |
| 5,096,654 | A | 3/1992 | Craggs et al. |
| 5,827,904 | A | 10/1998 | Hahn |
| 5,879,400 | A | 3/1999 | Merrill et al. |
| 6,165,220 | A | 12/2000 | McKellop et al. |
| 6,316,158 | B1 | 11/2001 | Saum et al. |
| 6,448,315 | B1 | 9/2002 | Lidgren et al. |
| 6,641,617 | B1 | 11/2003 | Merrill et al. |
| 6,852,772 | B2 | 2/2005 | Muratoglu et al. |
| 6,951,654 | B2 | 10/2005 | Malcolm et al. |
| 7,205,339 | B2 | 4/2007 | Muratoglu |

(Continued)

FOREIGN PATENT DOCUMENTS

| | | |
|---|---|---|
| EP | 0881919 A1 | 12/1998 |
| EP | 1457172 A1 | 9/2004 |

(Continued)

OTHER PUBLICATIONS

Ajandouz et al., Effects of pH on Caramelization and Maillard Reaction Kinetics in Fructose-Lysine Model Systems. Journal of Food Science. 2001;66(7):926-931.

(Continued)

*Primary Examiner* — Robert C Boyle
(74) *Attorney, Agent, or Firm* — McCarter & English, LLP

(57) ABSTRACT

The inventions provide methods of manufacturing peroxide cross-linked and high temperature melted polymeric material, for example ultra-high molecular weight polyethylene (UHMWPE) containing vitamin E, total joint implants with high wear resistance, high oxidation resistance, and very low concentration of residual by-products, as well as products made thereby.

18 Claims, 2 Drawing Sheets

(56) References Cited

U.S. PATENT DOCUMENTS

| | | |
|---|---|---|
| 7,381,752 B2 | 6/2008 | Muratoglu |
| 7,431,874 B2 | 10/2008 | Muratoglu et al. |
| 7,790,779 B2 | 9/2010 | Muratoglu |
| 7,833,452 B2 | 11/2010 | Muratoglu et al. |
| 7,858,671 B2 | 12/2010 | Merrill et al. |
| 8,133,501 B2 | 3/2012 | Li et al. |
| 8,232,322 B2 | 7/2012 | East et al. |
| 8,420,000 B2 | 4/2013 | Muratoglu et al. |
| 8,425,815 B2 | 4/2013 | Muratoglu et al. |
| 8,461,225 B2 | 6/2013 | Muratoglu et al. |
| 8,529,937 B2 | 9/2013 | Brunner et al. |
| 8,530,057 B2 | 9/2013 | Muratoglu et al. |
| 8,569,395 B2 | 10/2013 | Muratoglu et al. |
| 8,858,979 B1 | 10/2014 | Desjardins et al. |
| 8,933,145 B2 | 1/2015 | Oral et al. |
| 9,168,683 B2 | 10/2015 | Muratoglu et al. |
| 9,220,811 B2 | 12/2015 | Overstreet et al. |
| 9,273,189 B2 | 3/2016 | Muratoglu et al. |
| 9,370,878 B2 | 6/2016 | Muratoglu et al. |
| 9,433,705 B2 | 9/2016 | Muratoglu et al. |
| 9,445,901 B2 | 9/2016 | Tunc et al. |
| 9,681,683 B2 | 6/2017 | Esposti et al. |
| 9,731,047 B2 | 8/2017 | Oral et al. |
| 9,937,278 B2 | 4/2018 | Steinberg et al. |
| 9,968,709 B2 | 5/2018 | Muratoglu et al. |
| 10,220,547 B2 | 3/2019 | Muratoglu et al. |
| 10,967,100 B2 | 4/2021 | Oral et al. |
| 10,981,302 B2 | 4/2021 | Muratoglu et al. |
| 2002/0064653 A1 | 5/2002 | Ladika |
| 2002/0107330 A1 | 8/2002 | Pinchuk et al. |
| 2004/0156879 A1 | 8/2004 | Muratoglu et al. |
| 2004/0180072 A1 | 9/2004 | Tunc et al. |
| 2005/0048121 A1 | 3/2005 | East et al. |
| 2005/0090571 A1 | 4/2005 | Mehta et al. |
| 2006/0064653 A1 | 3/2006 | Zhang et al. |
| 2007/0059334 A1 | 3/2007 | Abt et al. |
| 2007/0077268 A1 | 4/2007 | King et al. |
| 2007/0114702 A1 | 5/2007 | Muratoglu et al. |
| 2007/0141106 A1 | 6/2007 | Bonutti et al. |
| 2007/0213835 A1 | 9/2007 | Wimmer et al. |
| 2007/0265369 A1 | 11/2007 | Muratoglu |
| 2007/0267030 A1 | 11/2007 | Muratoglu et al. |
| 2007/0293647 A1 | 12/2007 | McKellop et al. |
| 2008/0215142 A1 | 9/2008 | Muratoglu et al. |
| 2008/0319137 A1 | 12/2008 | Rufner et al. |
| 2009/0030524 A1 | 1/2009 | Schroeder et al. |
| 2009/0118390 A1 | 5/2009 | Abt et al. |
| 2009/0181253 A1 | 7/2009 | Michalik et al. |
| 2009/0243159 A1 | 10/2009 | Sun |
| 2009/0263319 A1 | 10/2009 | Wohabrebbi et al. |
| 2010/0190882 A1 | 7/2010 | Muratoglu et al. |
| 2010/0292374 A1 | 11/2010 | Bellare |
| 2011/0039014 A1 | 2/2011 | King |
| 2011/0040381 A1 | 2/2011 | Kidd et al. |
| 2011/0070454 A1 | 3/2011 | Gregg et al. |
| 2012/0041094 A1 | 2/2012 | Oral et al. |
| 2012/0046380 A1 | 2/2012 | Morrison et al. |
| 2012/0052292 A1 | 3/2012 | Pulapura et al. |
| 2012/0267819 A1 | 10/2012 | Freedman |
| 2013/0203885 A1 | 8/2013 | Muratoglu et al. |
| 2014/0024736 A1 | 1/2014 | Thomas et al. |
| 2014/0098001 A1 | 4/2014 | Van Oosterbosch et al. |
| 2014/0175693 A1 | 6/2014 | Liu |
| 2015/0151866 A1 | 6/2015 | Oral et al. |
| 2015/0190545 A1 | 7/2015 | Oral |
| 2015/0290280 A1 | 10/2015 | Petrak et al. |
| 2015/0314038 A1 | 11/2015 | Oral et al. |
| 2016/0215117 A1* | 7/2016 | Muratoglu .............. A61L 2/081 |
| 2016/0250779 A1 | 9/2016 | Muratoglu et al. |
| 2017/0049934 A1 | 2/2017 | Muratoglu et al. |
| 2017/0137603 A1 | 5/2017 | Morrison et al. |
| 2017/0259467 A1 | 9/2017 | Muratoglu et al. |
| 2018/0161480 A1 | 6/2018 | Oral et al. |
| 2018/0318468 A1 | 11/2018 | Oral et al. |
| 2019/0134273 A1 | 5/2019 | Oral et al. |
| 2019/0160207 A1 | 5/2019 | Suhardi et al. |
| 2019/0255744 A1 | 8/2019 | Muratoglu et al. |
| 2021/0228775 A1 | 7/2021 | Oral et al. |

FOREIGN PATENT DOCUMENTS

| | | |
|---|---|---|
| EP | 1779877 A1 | 5/2007 |
| EP | 2384774 A2 | 11/2011 |
| EP | 2833981 A2 | 2/2015 |
| WO | 1997/029793 A1 | 8/1997 |
| WO | 1999/029793 A1 | 6/1999 |
| WO | 2001/005337 A1 | 1/2001 |
| WO | 2001/080778 A1 | 11/2001 |
| WO | 2002/00274 A1 | 1/2002 |
| WO | 2002/048259 A2 | 6/2002 |
| WO | 2005/074619 A2 | 8/2005 |
| WO | 2005/110276 A1 | 11/2005 |
| WO | 2006/026040 A1 | 3/2006 |
| WO | 2007/024684 A2 | 3/2007 |
| WO | 2007/024689 A2 | 3/2007 |
| WO | 2007/056667 A2 | 5/2007 |
| WO | 2007/139744 A2 | 12/2007 |
| WO | 2008/092047 A1 | 7/2008 |
| WO | 2008/109098 A2 | 9/2008 |
| WO | 2010/096771 A2 | 8/2010 |
| WO | 2012/061499 A1 | 5/2012 |
| WO | 2013/151950 A1 | 10/2013 |
| WO | 2013/151960 A2 | 10/2013 |
| WO | 2013/170005 A1 | 11/2013 |
| WO | 2015/057943 A2 | 4/2015 |
| WO | 2017/083476 A1 | 5/2017 |
| WO | 2017/192347 A1 | 11/2017 |
| WO | 2019/046243 A2 | 3/2019 |

OTHER PUBLICATIONS

Atkinson et al., Materials for internal prostheses: the present position and possible future developments. Biomaterials. Apr. 1980;1(2):89-99.

Bourne, Prophylactic use of antibiotic bone cement: an emerging standard-in the affirmative. J Arthroplasty. Jun. 2004;19(4 Suppl 1):69-72.

Bragdon et al., A new pin-on-disk wear testing method for simulating wear of polyethylene on cobalt-chrome alloy in total hip arthroplasty. J Arthroplasty. Aug. 2001;16(5):658-65.

Chen et al., Photocrosslinking of Polyethylene. I. Photoinitiators, Crosslinking Agent, and Reaction Kinetics. Journal of Polymer Science Part A: Polymer Chemistry Edition. 1989;27(12):4051-4075.

Costa et al., Mechanisms of Crosslinking, Oxidative Degradation and Stabilization of UHMWPE. UHMWPE Biomaterials Handbook, Second Edition. Chapter 21, pp. 309-323, (2009).

Darouiche, Device-associated infections: a macroproblem that starts with microadherence. Clin Infect Dis. Nov. 1, 2001;33(9):1567-72.

De Kok et al., Reactivity of Peptides in the Maillard Reaction. Thermally Generated Flavors, Maillard, Microwave, and Extrusion Processes. American Chemical Society. Chapter 13, pp. 158-179, Nov. 30, 1993.

Eichner et al., Detection of Amadori Compounds in Heated Foods. Thermally Generated Flavors, Maillard, Microwave, and Extrusion Processes. American Chemical Society. Chapter 15, pp. 42-54, Nov. 30, 1993.

Fang et al., Processing and mechanical properties of HA/UHMWPE nanocomposites. Biomaterials. Jul. 2006;27(20):3701-7.

Gogia et al., Local antibiotic therapy in osteomyelitis. Semin Plast Surg. May 2009;23(2):100-7.

Irganox 1010, Phenolic Primary Antioxidant for Processing and Long-Term Thermal Stabilization, Ciba Specialty Chemicals, Inc. 2 pages, Aug. 1998.

John, Plastics Research, Evaluation of cross-linked UHMWPE with regards to its suitability as implant material for hip joint shells. Manfred H. Wagner. Polymer Technology/Plastics Technical Center, Berlin. 155 pages, Nov. 2003.

(56) References Cited

OTHER PUBLICATIONS

Kurtz et al., Vitamin-E Blended UHMWPE Biomaterials. UHMWPE Biomaterials Handbook, Third Edition, Ultra High Molecular Weight Polyethylene in Total Joint Replacement and Medical Devices. pp. 293-306, (2016).

Maillard et al., Chimie Organique. Comptes Rendus Hebdomadaires Des Seances de L'Academie des Sciences. Jan. 8, 1912;154(2):66-68.

Morshedian et al., Polyethylene Cross-linking by Two-step Silane Method: A Review. Iranian Polymer Journal. 2009;18(2):103-128.

Mortin et al., Rapid bactericidal activity of daptomycin against methicillin-resistant and methicillin-susceptible *Staphylococcus aureus* peritonitis in mice as measured with bioluminescent bacteria. Antimicrob Agents Chemother. May 2007;51(5):1787-94.

Muratoglu et al., Gradient crosslinking of UHMWPE using irradiation in molten state for total joint arthroplasty. Biomaterials. Feb. 2002;23(3):717-24.

Oral et al., A surface crosslinked UHMWPE stabilized by vitamin E with low wear and high fatigue strength. Biomaterials. Sep. 2010;31(27):7051-60.

Oral et al., Peroxide cross-linked UHMWPE blended with vitamin E. J Biomed Mater Res B Appl Biomater. Aug. 2017; 105(6):1379-1389.

R.T. Vanderbilt Company Inc., Comprehensive VAROX Peroxide Accelerator Product Guide. www.rtvanderbilt.com, 31 pages, Apr. 18, 2012.

R.T. Vanderbilt Company Inc., VAROX DBPH Liquid, Peroxide Accelerator, 2,5-dimethyl-2,5-di(t-butylperoxy)hexane. Chemicals Technical Data Sheet. 2 pages, Apr. 18, 2011.

Spellberg et al., Systemic antibiotic therapy for chronic osteomyelitis in adults. Clin Infect Dis. Feb. 1, 2012;54(3):393-407.

Stevens et al., An articulated antibiotic spacer used for infected total knee arthroplasty: a comparative in vitro elution study of Simplex and Palacos bone cements. J Orthop Res. Jan. 2005;23(1):27-33.

Suhardi et al., A Fully Functional Drug-Eluting Joint Implant. Nat Biomed Eng. 2017;1:0080.

Van De Belt et al., Infection of orthopedic implants and the use of antibiotic-loaded bone cements. A review. Acta Orthop Scand. Dec. 2001;72(6):557-71.

Van De Belt et al., Surface roughness, porosity and wettability of gentamicin-loaded bone cements and their antibiotic release. Biomaterials. Oct. 2000;21(19):1981-7.

International Search Report and Written Opinion for Application No. PCT/US2010/024935, dated Sep. 27, 2010, 13 pages.

International Search Report and Written Opinion for Application No. PCT/US2013/034887, dated Sep. 26, 2013, 6 pages.

International Search Report and Written Opinion for Application No. PCT/US2014/060865, dated Mar. 13, 2015, 12 pages.

International Search Report and Written Opinion for Application No. PCT/US2016/061256, dated Feb. 9, 2017, 10 pages.

International Search Report and Written Opinion for Application No. PCT/US2017/029789, dated Jul. 31, 2017, 9 pages.

International Search Report and Written Opinion for Application No. PCT/US2018/048256, dated Mar. 13, 2019, 16 pages.

International Search Report and Written Opinion for Application No. PCT/US2019/060904, dated Jan. 28, 2020, 6 pages.

International Search Report and Written Opinion for Application No. PCT/US2020/024497, dated Jul. 2, 2020, 22 pages.

U.S. Appl. No. 13/202,014, filed Oct. 31, 2011, U.S. Pat. No. 8,933,145, Issued.

U.S. Appl. No. 14/584,519, filed Dec. 29, 2014, U.S. Pat. No. 9,731,047, Issued.

U.S. Appl. No. 15/653,977, filed Jul. 19, 2017, 2018-0161480, Abandoned.

U.S. Appl. No. 16/229,400, filed Dec. 21, 2018, U.S. Pat. No. 10,967,100, Issued.

U.S. Appl. No. 17/222,398, filed Apr. 5, 2021, 2021-0228775, Published.

U.S. Appl. No. 14/389,852, filed Oct. 1, 2014, 2016-0215117, Abandoned.

U.S. Appl. No. 15/774,860, filed May 9, 2018, 2018-0318468, Published.

\* cited by examiner

DI-CUMYL PEROXIDE CROSSLINKING OF UHMWPE

This application claims priority to U.S. Provisional Application Ser. No. 63/169,120, filed on Mar. 31, 2021, which is hereby incorporated by reference in its entirety.

BACKGROUND OF THE INVENTIONS

The inventions provide methods of manufacturing peroxide cross-linked and high temperature melted polymeric material, for example ultra-high molecular weight polyethylene (UHMWPE) containing vitamin E, total joint implants with high wear resistance, high oxidation resistance, and very low concentration of residual by-products, as well as products made thereby.

The mechanical properties of the consolidated solid forms of polymeric resin are dependent on the consolidation method and conditions. In addition, one or more of the mechanical properties can be enhanced further by further treatment of the consolidated form, for example by peroxide cross-linking (U.S. Application No. 61/756,596) or high temperature melting (U.S. Patent Publication No. 2012/0041094). These methods may include exposure to temperatures above the melting point of polyethylene, especially temperatures close to or greater than 200° C. for prolonged periods of time also known in the art as high temperature melting (HTM).

During the consolidation and peroxide crosslinking of UHMWPE, there may be variable amounts of residual by-products generated by the peroxide chemistry in the polymer. Some or none of these residual by-products are desirable in the final material. For instance, permanent medical implants fabricated from peroxide crosslinked UHMWPE should not elute high concentrations of toxic residual byproducts during in-vivo service. Therefore, it is important to reduce the concentration of toxic residual byproducts in peroxide crosslinked UHMWPE as much as possible.

One peroxide used in crosslinking of UHMWPE is di-cumyl peroxide (DCP).

Peroxide cross-linking approaches are disclosed in U.S. Pat. No. 10,981,302 and U.S. Patent Publication No. 2016/0215117, which are hereby incorporated by reference. High temperature melting approaches are disclosed in U.S. Pat. No. 9,731,047, which is hereby incorporated by reference.

This inventions provide improved methods of manufacturing peroxide cross-linked and high temperature melted polymeric material total joint implants.

BRIEF SUMMARY OF THE INVENTIONS

Polyolefins, such as UHMWPE, are commonly crosslinked using peroxides. Di-cumyl peroxide (DCP) is one the most commonly used peroxides for this purpose. We discovered that peroxide crosslinking of UHMWPE results in an oxidatively unstable polymer and that adding an antioxidant, such as vitamin-E or Irganox 1010 (Pentaerythritol tetrakis(3,5-di-tert-butyl-4-hydroxyhydrocinnamate), makes the material resistant to oxidation. In addition, peroxide crosslinking results in by-products that may not be desirable. The main by-products of DCP crosslinking are acetophenone (ACP), alpha-methylstyrene, and cumyl alcohol and these compounds can be found in DCP crosslinked UHMWPE. Many of these by-products are volatile. We also discovered that subjecting the DCP crosslinked UHMWPE to high temperature melting increases the toughness of the material and helps in extracting these volatile by-products. For example, acetophenone boils at 202° C. Heating DCP crosslinked UHMWPE during or after crosslinking to above 202° C. accelerates the removal of acetophenone. However, depending on the thickness of the DCP crosslinked UHMWPE, the removal of ACP may take a very long time. Exposure to high temperatures for long durations would result in excessive chain scission and decrease the wear resistance of the polymer. A delicate balance needs to be established during the high temperature heat treatment to decrease the concentration of by-products to or below the desired levels without substantially compromising wear resistance.

DETAILED DESCRIPTION OF THE INVENTIONS

Figure 1:
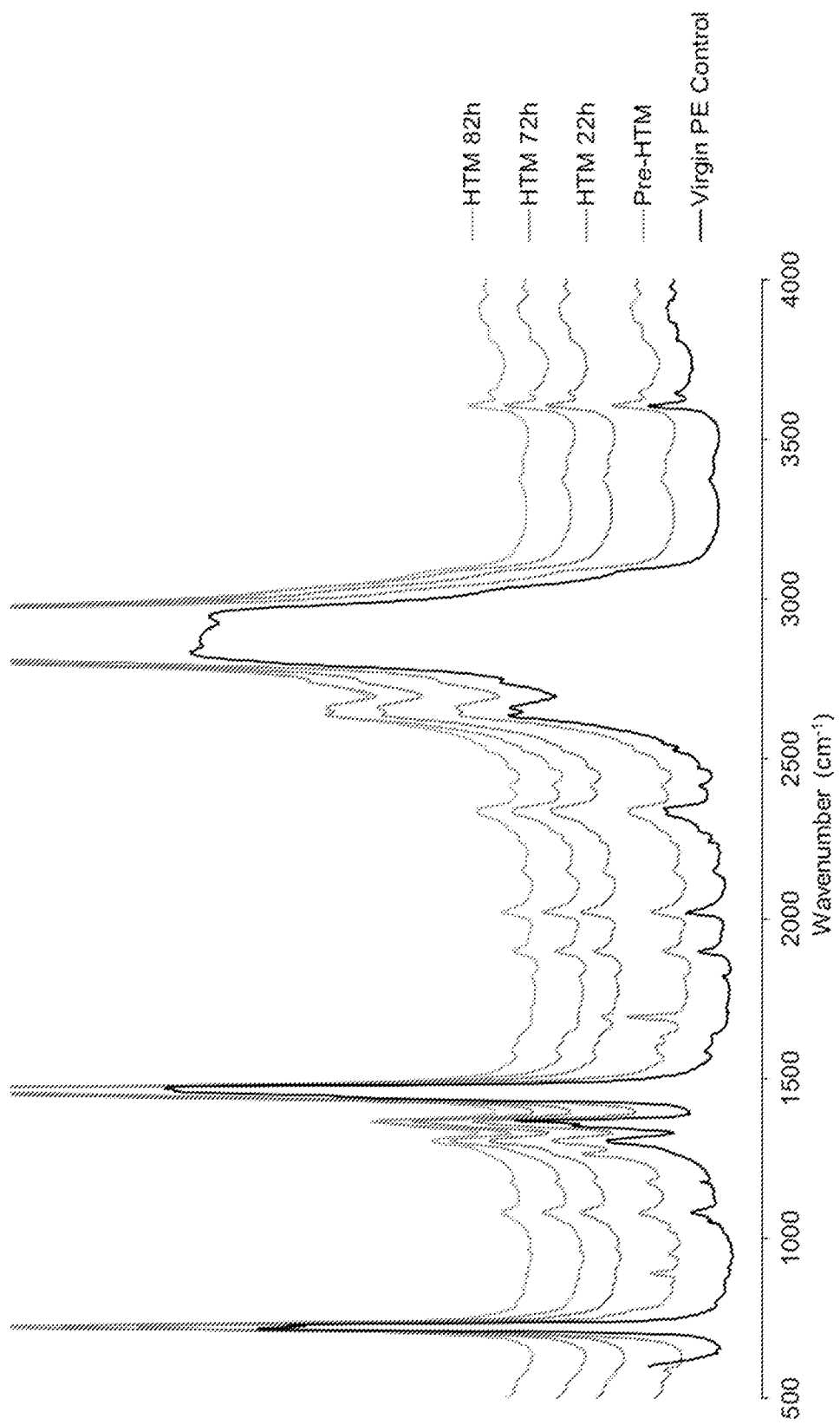
FIG. 1 shows FTIR spectra of various UHMWPE formulations. The characteristic absorbance for acetophenone (ACP) is located at 1674 $cm^{-1}$-1712 $cm^{-1}$. Before the HTM treatment the peroxide crosslinked UHMWPE shows a strong ACP peak, while after the 72-hr and 82-hr HTM treatments the ACP peak is not visible.

The term "about" in the context of numerical values and ranges refers to values or ranges that approximate or are close to the recited values or ranges such that the inventions can perform as intended, such as having a desired rate, amount, degree, increase, decrease, concentration, or time, as is apparent from the teachings contained herein. Thus, this term encompasses values beyond those simply resulting from systematic error.

Blending: DCP is solid at room temperature; therefore, it can be solubilized in a solvent before it is blended with UHMWPE powder. The benefit of dissolving DCP in a solvent is that it also results in a highly uniform DCP/UHMWPE blend. In fact, DCP solution diffuses into the UHMWPE particles during blending. When the solvent is evaporated from the blend, during the blending process, DCP will remain associated with the UHMPE particles and help prevent loss of uniformity of the blend during storage. Vitamin E, one of the preferred antioxidants, is a viscous liquid at room temperature. Vitamin E is also solubilized in a solvent to facilitate the blending with the UHMWPE particles. Similar to DCP, vitamin E is also compatible with and associated with UHMWPE particles after the solvent is evaporated during the blending process. In one embodiment, DCP and vitamin-E are dissolved in a solvent, for instance acetone or alcohol or other solvents or mixtures of solvents, and the resulting solution is mixed with UHMWPE powder in a mixer blending machine.

First, the UHMWPE powder is placed in a mixer blending machine. While the said UHMPWE is agitated in the blending machine the DCP and vitamin-E solution is placed into the chamber containing UHMWPE powder, for instance by injecting through a port. The mixture is agitated and at some time during the agitation vacuum is applied to the chamber to evaporate and remove the solvent(s). Preferably no excess heat is applied to the chamber to minimize premature dissociation of DCP and the resulting crosslinking of UHMWPE. Preferably the temperature inside the blending chamber is kept low to minimize DCP dissociation, which is also known in the art as decomposition. The half-life temperatures of DCP are 61° C. (for 10 hours), 80° C. (for 1 hour) and 120° C. (for 1 minute); therefore, it is preferable to maintain the temperature inside the blending chamber at a temperature lower than 120° C. to minimize peroxide dissociation and UHMWPE crosslinking. The described blending method results in a uniform blend of DCP and vitamin-E in UHMWPE.

One optimized formulation of GUR1020 UHMWPE contains 10,000±500 ppm of DCP, and 2000±500 ppm of synthetic vitamin E. In some embodiments the blending is done in a stepwise fashion, whereby DCP, which is dissolved in a solvent and the antioxidant, which is also dissolved in a solvent are added to the UHMWPE powder either together or separately. The stepwise blending can be done in any order, that is DCP solution is added first followed by antioxidant solution or vice-versa. In some embodiments both solutions are added to the UHMWPE powder together. In certain embodiments the solutions are added to the UHMWPE powder inside the mixer blending machine or they are added before the powder is placed in the mixer blending machine. In some embodiments, there can be multiple steps of adding UHMWPE powder, DCP solution, and antioxidant solution, which can be repeated until the desired concentration of DCP and antioxidant in UHMWPE is reached.

Molding: The DCP/Vitamin E/UHMWPE blend is direct compression molded in a mold tool at a temperature above the melting point of UHMWPE. Molding involves pouring the blend into the cavity of the mold tool, placing the plunger inside the cavity, applying force on the plunger, heating the mold to a molding temperature at a certain heating rate, holding the mold tool under force at the desired molding temperature, and cooling the mold before removing the force, removing the plunger, and removing the molded article from the mold cavity. If the heating rate is too slow, premature crosslinking of UHMWPE powder will occur and that crosslinking will to some degree inhibit consolidation of the powder.

Preferably the molding is at between 150° C. and 250° C. or higher for about 30 minutes to 2 hours. During molding the mold tool is heated to the molding temperature over a period of 10 minutes to 2 hours. In some embodiments the heating time is shorter than 10 minutes or longer than 2 hours depending on the size of the sample that is being molded. Preferably heating time is 30 minutes to 1 hour. Preferably the height of the molded article is less than 3 inches, is less than 2.5 inches, is less than 1.5 inches. More preferably the molded article is slightly larger than a medical implant so that the molded piece can be machined into that medical implant shape after high temperature melting.

High temperature melting: The molded DCP/vitamin E/UHMWPE blend or DCP-crosslinked vitamin E blend is heated to at or above 200° C. The heating rate is controlled to limit the heterogeneity through the molded blend. The heating can be done to a temperature around 250, 260, 270, 280, 290 or 300° C. for an optimum period to increase the elongation-at-break to about 400%. The duration changes with the thickness of the molded blend; thicker samples may require longer duration at temperature. Cooling rate can be controlled to limit dimensional stability. Multiple heating and cooling rates can be used during the process.

Vitamin E: The definition refers to what is known in the art as a collective of fat-soluble vitamins with distinct antioxidant activity, comprising mainly alpha-tocopherol and its derivatives, isomers and enantiomers such as delta-tocopherol, beta-tocopherol, gamma-tocopherol, alpha-tocotrienol, beta-tocotrienol, gamma-tocoptrienol, tocopherol acetate, tocopherol succinate or a combination thereof.

Oxidation of the polymer, which results in carbonyl-containing compounds on the polymer can be measured by Fourier Transform Infrared Spectroscopy (FTIR), for example by guidance described in American Society for Testing and Materials 2102-17: Standard Guide for Evaluating the Extent of Oxidation in Polyethylene Fabricated Forms Intended for Surgical Implants. Accelerated aging can be performed to compare the resistance of polyethylene materials to oxidation by, for example methods described in ASTM F2003-02R15 Standard Practice for Accelerated Aging of Ultra-High Molecular Weight Polyethylene after Gamma Irradiation in Air. The oxidation index is commonly measured at different locations throughout a cross-section and reported as an average over a given depth, or a maximum oxidation observed in the material. A 'non-oxidized material' or a 'a material with no detectable oxidation' generally exhibits a maximum oxidation index level below 0.1, an 'oxidation-resistant material' generally exhibits a maximum oxidation index level below 0.5, an 'oxidized material' exhibits am index between 0.5 and 1.0, and a 'highly oxidized material' exhibits an index above 1.0 when analyzed according to these methods after 2 weeks of accelerated aging at 5 atm. of oxygen at 70° C.

All numerical limits and ranges set forth herein include all numbers or values thereabout or there between of the numbers of the range or limit. The ranges and limits described herein expressly denominate and set forth all integers, decimals and fractional values defined and encompassed by the range or limit. Thus, a recitation of ranges of values herein are merely intended to serve as a shorthand method of referring individually to each separate value falling within the range, unless otherwise indicated herein, and each separate value is incorporated into the specification as if it were individually recited herein.

The inventions are further described by the following Examples, which are illustrative of the many embodiments and aspects of the inventions, but do not limit the inventions in any manner. The order and manner of performance of the below examples can be altered or combined as determined by the person of skill in the art in view of the teachings contained herein.

Example 1—Slow Cool to Avoid Dimensional Instability

We discovered that if the molded articles that are subjected to high temperature melting are cooled at a rapid rate the implants machined from these said articles display some degree of dimensional instability. That is, implant machined after the heat treatment could lose their dimensional tolerances. To minimize the dimensional changes after machining, heat treated article is subjected to slow cooling. This could be achieved by using an extremely slow cooling rate. Another way of achieving a dimensionally stable machined implant is to cool the article to a temperature above the crystallization temperature, followed by soaking/holding at around that temperature until the temperature is somewhat uniform within the article, followed by cooling to a temperature at or below the crystallization temperature, followed by soaking holding at around that temperature until the temperature is somewhat uniform within the article, followed by cooling to room temperature.

Example 2—Acetophenone Quantification with FTIR

The blocks are cut in half with a band saw, and thin films (~150 μm in thickness) are cut from the newly exposed surface using a sledge microtome for Fourier Transform Infrared (FTIR) analysis. A thin film is loaded onto an FTIR spectrophotometer with a microscope attachment (670IR/620, Varian Inc., Palo Alto CA), and sequential 100 μm$^2$ square sections of the film is analyzed from 4000-400 cm$^{-1}$ wavenumbers at 8 cm$^{-1}$ resolution from the edge of the thin film that corresponded to a free surface of the original block to a location on the thin film that corresponded to the body center of the original block. Acetophenone levels are quantified and expressed as an ACP index calculated by integrating the absorbance over 1674 cm$^{-1}$-1712 cm$^{-1}$ (ACP peak) and subtracting the baseline below that absorbance peak. The ACP indices are normalized to the polyethylene absorbance over 1330 cm$^{-1}$-1390 cm$^{-1}$ after subtracting the baseline below that absorbance peak. The normalization is to account for any variation in thin film thickness. FIG. 1 shows the variation in the acetophenone characteristic absorption collected from the body center of samples that were subjected to different high temperature melting cycles. In general, the acetophenone characteristic absorption decreases with increasing duration of the high temperature melting treatment. Thinner samples display lower acetophenone absorption as expected.

Figure 2:
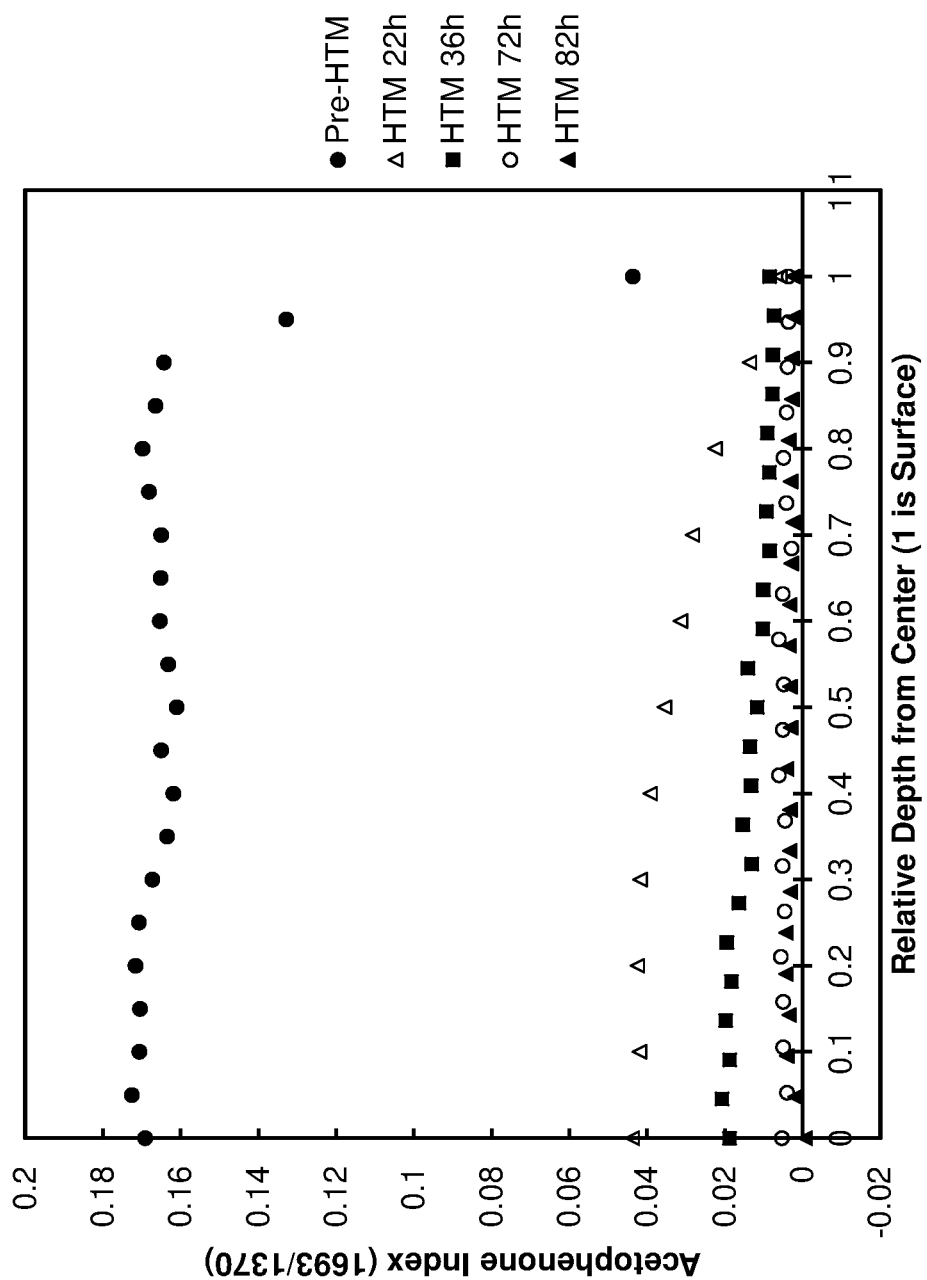
FIG. 2 visualized the acetophenone (ACP) index values as a function of distance from the body center to the free surface of the test samples where the ACP index is calculated from FTIR spectra collected form thin films machined from the test samples. Depth is normalized to total distance from the body center to free surface of each test sample. Normalized depth from center value 1 represents the surface. Before HTM treatment the peroxide crosslinked UHMWPE shows a strong ACP index. Following the 72-hr and 82-hr HTM treatment the index value decreases to below 0.01, well below the target of <0.03.

FIG. 2 shows the variation in the acetophenone index as a function of distance from the body center to the surface of the test samples treated with high temperature melting. With increasing duration of the high temperature melting treatment the acetophenone index also decreases.

Example 3—Target Properties and their Optimization

The target properties of HTM treated peroxide cross-linked UHMWPE/vitamin-E blend are as follows: (i) ACP index <0.03; (ii) EAB 350-400%; (iii) UTS>43 MPa; (iv) YS>17 MPa; (v) POD<3 mg/MC; and (vi) Izod>70 kJ/m$^2$. One optimum material will need to have sufficient acetophenone by-product removed by bringing the ACP index to below 0.03. While higher temperatures and longer durations during HTM processing increases the removal of ACP, it also adversely affects other properties, such as increasing wear rate. Elongation at break (EAB) is directly proportional to wear rate; therefore, EAB values below 400% are preferred to keep the wear rate low. For example, the 72 hr HTM cycle lowers the ACP index to below 0.03 and keeps the EAB also below 400%. In contrast the 82-hr cycle results in EAB values above 400% and compromises the wear rate.

Example 4—Optimum HTM Cycle

The optimum HTM cycle recipe for a sample with a height or thickness of about 2.4 inches or less is about 72 hours long. The steps are as follows: heat to 275° C. and hold for 4 h followed by heat to 295° C. and hold for 8 h followed by cool to 275° C. and hold for 43 h followed by cool to 130° C. and hold for 5 h followed by cool to 115° C. and hold for 5 h followed by cool to 105° C. and hold for 5 h followed by cool to 40° C. and hold 2 h. The temperatures listed can be 5° C. above or below the target temperatures listed. The hold durations can be half hour longer or shorter. It is critical that the heating duration at 295±5° C. is not any longer than 9 hours to avoid degradation of wear properties. Also, it is critical to keep the sample above 250° C. for at least 50 hours to ensure that the acetophenone index is below 0.03 and less than 70 hours to ensure that wear rate is not degraded. In some applications higher acetophenone index values are tolerated, for instance acetophenone index of 0.06 or less. For these applications the preforms can be kept above 250° C. for less than 70 hours or less than 50 hours, which will also result in lower wear rate and lower ductility as measured by elongation at break in a tensile test.

Example 5—Preparation of Tibial Knee Inserts and Characterization

Tibial Knee Inserts were fabricated from ultra-high molecular weight polyethylene material (GUR 1050 UHMWPE powder) blended with alpha tocopherol (Vitamin E). Alpha tocopherol (DSM, Heerlen, Netherlands) and di-cumyl peroxide (Arkema, King of Prussia, PA) were dissolved in acetone. A 37.5 kg blend was prepared by mixing UHMWPE powder with an acetone solution of vitamin-E and di-cumyl peroxide, where the solution contained 38 g of vitamin-E and 208.95 g of di-cumyl peroxide in 1 liter of acetone. Alternatively, a 25 kg blend can be prepared by mixing UHMWPE powder with an acetone solution of vitamin-E and di-cumyl peroxide, where the solution contains 25.35 g of vitamin-E and 139.3 g of di-cumyl peroxide in 1 liter of acetone. The acetone solution was blended with GUR 1050 powder (Ticona, Florence KY). Blending of all materials was completed within an applied vacuum, and the acetone was removed from the materials by the vacuum. The remaining blended materials were then compression molded with applied heat and pressure (during molding the mold is heated to about 224° C. and the cavity is pressurized to about 6.9 MPa), to consolidate the material to a slab per manufacturing material specification, and the compression molded slabs were then machined to create implant preforms. The preforms were divided into two groups and subjected to a high temperature melt process where the preforms were heated in a nitrogen gas convection oven. One group was heated (high temperature melting—HTM) for 22 hours and the other for 72 hours. The samples which underwent peroxide crosslinking ("PRX") and the 72-hour HTM cycle time are referred to as "PRX 72 hr HTM samples," and the samples which underwent the 22-hour HTM cycle time are referred to as "PRX 22 hr HTM samples." The tables below use this nomenclature.

The HTM step was carried out by placing the samples in an oven, which was continuously purged with nitrogen gas to reduce the oxygen content in the oven and minimize oxidation of the preforms. The HTM step for the PRX 72 hr HTM samples was as follows: Set the oven temperature to about 270° C. and hold for about 5 hours, then set the oven temperature to about 288° C. and hold for about 8 hours, then set the oven temperature to about 270° C. and hold for about 44 hours, then set the oven temperature to about 130° C. and hold for about 6 hours, and finally set the oven temperature to about 115° C. and hold for about 9 hours. The HTM step for the PRX 22 hr HTM samples was as follows: Set the oven temperature to 250° C. and hold for 1.5 hours, then set the oven temperature to 300° C. and hold for 4 hours, then set the oven temperature to 250° C. and hold for 12 hours and finally set the oven temperature to 55° C. and hold for 4.5 hours.

After high temperature melt processing, the preforms were machined into the final Tibial Insert geometry or the corresponding test sample geometries, and then cleaned, packaged, and gamma irradiated with 25-40 kGy for sterilization. Some of the test samples were accelerated aged in 5 atm of pure oxygen at 70° C. for 2 weeks per ASTM F2003-02R15. The aged and unaged test samples were then characterized for mechanical properties. Material characterization results are provided for the PRX 22 hr HTM material in Table 1.

TABLE 1

Material characterization results of PRX 22 hr HTM material with respect to Appendix 2 of the FDA Guidance document "Characterization of Ultrahigh Molecular Weight Polyethylene (UHMWPE) Using in Orthopedic Devices".

| Property and Standard | Test Description | PRX 22 hr HTM material |
|---|---|---|
| Tensile Properties per ASTM D638-03 | Ultimate Tensile Strength (MPa) | Unaged: 49<br>Aged: 50.2 |
| | Tensile Yield Strength (MPa) | Unaged: 19.5<br>Aged: 20.8 |
| | Elongation (%) | Unaged: 359<br>Aged: 359 |
| Elastic Modulus | Elastic Modulus | Unaged: 712 +/− 65<br>Aged: 698 +/− 65 |
| Crystallinity, Melting Temperature per ASTM F2625-10 | Percent Crystallinity | Unaged: 51.24<br>Aged: 51.53 |
| | Melting Temperature (° C.) | Unaged: 125.05<br>Aged: 124.7 |
| Impact Resistance per ASTM D256-10 | Izod Impact Strength (kJ/m$^2$) | Unaged: 77.28<br>Aged: 76.63 |
| Trans-vinylene index per ASTM F2381-19 | t-Vinylene Content, Max (TVI) | Unaged: .025<br>Aged: .023 |
| Post-accelerated Aging; Maximum Oxidation Index per ASTM 2103-15 | Oxidation Index Surface (SOI) | Unaged: .017<br>Aged: .028 |
| | Max (MOI) | Unaged: .027<br>Aged: .077 |
| | Bulk (BOI) | Unaged: .013<br>Aged: .02 |
| Density per ASTM D1505-03 | Density (kg/m$^3$) | Unaged: 929<br>Aged: 930 |
| Crosslink Density per ASTM F2214-16 | Swell Ratio | Unaged: 2.785<br>Aged: 2.880 |
| | Crosslink Density (mol/dm$^3$) | Unaged: .246<br>Aged: .229 |
| | Molecular Weight Between Crosslinks (g/mol) | Unaged: 3744<br>Aged: 4016 |
| Fatigue Resistance per ASTM E647-15 | Fatigue Crack Propagation, $\Delta K_{inception}$ MPa(m)$^{1/2}$ | Unaged: 0.96<br>Aged: 1.0 |
| Free Radical Concentration | Free Radical Content (spins/g) | Unaged: 1.4E+16<br>Aged: 1.5E+15 |

Knee Simulator Wear Testing-Tibial Inserts: The subject Tibial Inserts with PRX 22 hr HTM components were gamma sterilized with 25-40 kGy and accelerated aged in 5 atm of pure oxygen at 70° C. for 2 weeks per ASTM F2003-02R15. ISO standard 14243-3:2014 simulated gait was produced using Flexion/Extension, Anterior/Posterior Translation, Internal/External Rotation, and Axial Load. The Axial Load was scaled to a maximum of 3200 N (higher than the 2600N maximum load in ISO 14243-3).

Knee Simulator Wear Testing: Knee Simulator Wear Testing per ISO 14243-3 was completed. Testing was conducted on a 6-station knee simulator (AMTI, Watertown MA). Six aged, subject Tibial Inserts were tested through 5 million cycles (MC) of simulated gate per ISO 14243-3 in bovine serum. Knee simulator wear results showed a wear rate of 10.6±0.7 mg/MC.

Wear Particulate Characterization: A review of the literature has found that it is particles in the range of 0.1-10 μm which are of concern because they may lead to osteolysis. A high number/concentration of particles (greater than $1 \times 10^{10}$ per gram of tissue) is needed in the critical phagocytosable size range (0.1-10 μm), to cause macrophage-induced osteolysis. Osteolysis was found to be rare in patients with a wear rate of less than 80 mm$^3$ per year for minimum duration 10 years; therefore, the acceptance criterion for total volume of particle debris in the critical size range is a maximum of 800 mm$^3$.

Table 2 lists the overall weight change in the tibial inserts after 5MC of Knee Simulator Wear Testing. This weight change was used to calculate the volume of wear debris generated during testing, multiplying the total weight change of the component by the density of the material as shown below:

$$\text{Volume}_{wear\ particles} = (\text{Total Weight Change}) * (\text{Material Density})$$

TABLE 2

Total Sample Weight Change from 5MC of Knee Simulator Wear Testing

| Aged Sample Description | Sample # | Total Sample Weight Change (mg) | Material Density (mg/mm³) | Total Volume of Wear Particles (mm³) | Total Volume <800 mm³ |
|---|---|---|---|---|---|
| PRX 22 hr HTM Samples | Sample 1 | −58.47 | 0.9411 | 62.15 | Yes |
| | Sample 2 | −62.00 | | 65.91 | Yes |
| | Sample 3 | −55.66 | | 59.17 | Yes |
| | Sample 4 | −55.57 | | 59.07 | Yes |
| | Sample 5 | −54.99 | | 58.45 | Yes |
| | Sample 6 | −49.06 | | 52.15 | Yes |

The total volume of wear debris per year can be approximated using the number of average steps per year multiplied by the wear volume per cycle from knee simulator testing. Using an average of 4,774 steps per day, or 1.7M steps per year, multiplied by the wear volume per cycle from the Knee Simulator testing approximates the average wear volume per year. Table 3 lists the average wear volume per year based on 4,774 steps per day (assumes 1 step is equal to one Knee Simulator Wear cycle).

TABLE 3

Approximate average wear volume per year based on 4774 steps per day.

| Aged Sample Description | Sample # | Total Volume of Wear Particles (mm³) | Volume per Cycle of Testing | Volume per Year (4774 Cycles per day) (mm³) | <80 mm³/year of wear volume |
|---|---|---|---|---|---|
| PRX 22 hr HTM Samples | Sample 1 | 62.15 | 1.24E−05 | 21.36 | Yes |
| | Sample 2 | 65.91 | 1.32E−05 | 22.65 | Yes |
| | Sample 3 | 59.17 | 1.18E−05 | 20.33 | Yes |
| | Sample 4 | 59.07 | 1.18E−05 | 20.30 | Yes |
| | Sample 5 | 58.45 | 1.17E−05 | 20.09 | Yes |
| | Sample 6 | 52.15 | 1.04E−05 | 17.92 | Yes |

The approximate Wear Volume per year for all samples was found to be below 80 mm³ per year of wear, (shown in Table 2 and Table 3), and the PRX 22 hr HTM tibial inserts are below the wear volume per year value which was found to have rare occurrence of osteolysis by Nine et. al., *Materials* (Basel) 2014 February; 7(2): 980-1016. Published online 2014 Feb. 10. doi: 10.3390/ma7020980.

Mode III Wear: Mode III knee simulator wear was conducted utilizing scratched femoral components. The same worst-case sizing, and worst-case materials which were used in knee simulator testing with smooth femurs were utilized in Mode III testing, along with the same set-up and 3200N max load. The scratched femoral components resulted in a roughly 60% increase in overall wear of the PRX 22 hr HTM tibial inserts: 16.7±2.0 mg/MC during this aggressive testing vs. 10.6±0.7 mg/MC against clean femoral components.

Mechanical Properties of Unaged PRX 22 hr and 72 hr HTM:

TABLE 4

Mechanical properties of PRX 22 hr HTM and those of PRX 72 hr HTM.

| | PRX 22 hr HTM | PRX 72 hr HTM | p-values |
|---|---|---|---|
| Accelerated Aging | Unaged | Unaged | NA |
| HTM duration (hrs.) | 22 | 72 | NA |
| Gamma Sterilization | No | No | NA |
| EAB (%) | 358 ± 18 | 381 ± 3.1 | 0.027* |
| UTS (MPa) | 51.1 ± 1.3 | 52.3 ± 0.5 | 0.27 |
| YS (MPa) | 18.9 ± 0.2 | 22.3 ± 7.4 | 3.9E−11* |
| Izod (kJ/m²) | 83.8 ± 1.1 | 90 ± 2.5 | 0.0032* |

Example 6—Residual Byproduct Quantification

Toxicological risk assessment of five previously characterized byproducts, per Sayoun, J; Crepet A; Gouanve F; Keromnes L; Espuche E. 2017. "Diffusion mechanism of byproducts resulting from the peroxide crosslinking of polyethylene." J. Appl. Polym. Sci. 44525. doi: 10.1002/APP.44525, was carried out following ISO 10993-17:2002. Quantification was based on the maximum amount of chemical exposures from the anticipated maximum number of implants a patient may receive (in this case, 4 implants). An exhaustive literature search for toxicity data was conducted specific to each chemical of interest. This was accomplished via ToxPlanet (a federated search engine that extracts the content from 500+ websites). Biocompatibility endpoints were determined based on ISO 10993-1:2018 and recent United States Food and Drug Administration (US Food and Drug Administration 2016a. "Use of International Standard ISO-10993, 'Biological evaluation of medical devices—Part 1: Evaluation and testing within a risk management process': Guidance for Industry and Food and Drug Administration Staff." Center for Devices and Radiological Health (CDRH), 68p). These endpoints include chronic toxicity, reproductive and developmental toxicity, genotoxicity, carcinogenicity, and sensitization.

For chemicals which the exhaustive literature search did not yield toxicity data, in silico analysis for mutagenicity was conducted. The in silico methods utilized an expert-rule-based program (Toxtree version 3.1.0; Ideaconsult Ltd., 2018) and the statistics-based program VEGA version 1.2.8 and Benfenati, E; Manganaro, A; Gini, G. 2013. "VEGA-QSAR: AI inside a platform for predictive toxicology." In CEUR Workshop Proceedings, Volume 1107: Proceedings of The Second Workshop on Popularize Artificial Intelligence, (PAI 2013), Turin, Italy), consistent with the International Council for Harmonisation of Technical Requirements for Pharmaceuticals for Human Use (ICH) and US FDA guidelines for the assessment of DNA reactive impurities in pharmaceuticals (M7 guidelines; International Council for Harmonisation of Technical Requirements for Pharmaceuticals for Human Use (ICH). 2017a. "ICH Harmonised Guideline: Assessment and Control of DNA Reactive (Mutagenic) Impurities in Pharmaceuticals to Limit Potential Carcinogenic Risk M7(R1) (Current Step 4 Version); US Food and Drug Administration (US FDA 2018. "Guidance for Industry: M7(R1) Assessment and Control of DNA Reactive (Mutagenic) Impurities in Pharmaceuticals to Limit Potential Carcinogenic Risk." Center for Drug Evaluation and Research (CDER), Center for Biologics Evaluation and Research (CBER)).

The allowable limit (AL) was calculated using the no-observed-adverse-effect level (NOAEL) limits ascertained from the literature search and in silico methods described above. The NOAELs were then adjusted by the average body weight (BW) for adult males (70 kg) and adult females (58 kg). Following the recommendations of ISO 10993-17 and ICH Q3C(R7) (International Organization for Standardization (ISO). 2002. "ISO 10993-17: Biological Evaluation of Medical Devices—Part 17: Establishment of Allowable Limits for Leachable Substances." ISO 10993-17: 2002; International Council for Harmonisation of Technical Requirements for Pharmaceuticals for Human Use (ICH). 2018. "ICH Harmonised Guideline: Impurities: Guideline for Residual Solvents Q3C(R7) (Current Step 4 Version)."), the values were then adjusted by a series of uncertainty factors (UFs). $UF_1=10$ to account for interindividual variation; $UF_2=5$ for extrapolation of effects from rats to humans; $UF_3=10$ to account for extrapolation from an oral exposure study to systemic exposure risk associated with an implanted device; $UF_4=5$ to account for extrapolation of results from a 90-day toxicity study in rodents to lifetime exposure associated with a permanent implant; and $UF_5=10$ to account for extrapolation of a lowest-observed-adverse-effect level (LOAEL) to a NOAEL, if needed.

The equation had the following generalized form:

$$AL = NOAEL \frac{mg}{kg*day} * BWkg * \left(\frac{1}{UF_1*UF_2*UF_3*UF_4*UF_5}\right)$$

For example, the NOAEL for dicumyl peroxide (CAS No. 80-43-3) was documented as 80 mg/kg-day. As the NOAEL was available, $UF_5$ was not required. Subsequently, the final AL calculations were:

$$AL_{male} = 80\frac{mg}{kg*day} * 70\,kg * \left(\frac{1}{10*5*10*5}\right) = 2.24\frac{mg}{day} = 2{,}240\frac{\mu g}{day}$$

$$AL_{female} = 80\frac{mg}{kg*day} * 52\,kg * \left(\frac{1}{10*5*10*5}\right) = 1.86\frac{mg}{day} = 1{,}860\frac{\mu g}{day}$$

In cases in which insufficient toxicological data were available to evaluate the safety of a compound, but the compound was identified as potentially genotoxic by in silico analysis, the concept of a Threshold of Toxicological Concern (TTC) was applied (corresponding to a theoretical 10-5 excess lifetime cancer risk). For chemicals predicted to be non-mutagens in accordance with ICH and US FDA guidance for assessment of DNA reactive impurities in pharmaceuticals (ICH of Technical Requirements for Pharmaceuticals for Human Use. 2017a. "ICH Harmonised Guideline: Assessment and Control of DNA Reactive (Mutagenic) Impurities in Pharmaceuticals to Limit Potential Carcinogenic Risk M7(R1) (Current Step 4 Version)."; US Food and Drug Administration (US FDA). 2018. "Guidance for Industry: M7(R1) Assessment and Control of DNA Reactive (Mutagenic) Impurities in Pharmaceuticals To Limit Potential Carcinogenic Risk." Center for Drug Evaluation and Research (CDER), Center for Biologics Evaluation and Research (CBER)), the Revised Cramer Classification decision tree approach to assign default human threshold values (Cramer, G M; Ford, R A; Hall, R L. 1978. "Estimation of toxic hazard—A decision tree approach." Food Cosmet. Toxicol. 16(3):255-276; Munro, I C; Ford, R A; Kennepohl, E; Sprenger, J G. 1996. "Correlation of structural class with no-observed effect levels: A proposal for establishing a threshold of concern." Food Chem. Toxicol. 34(9):829-867) were relied upon. In total, 5 compounds were identified as potential chemical exposures and byproducts of the inventions. Their exposure limits, based on the methods described above, are detailed in Table 5.

TABLE 5

Allowable Limits of Potential Chemical Exposures from Peroxide-Crosslinked Polyethylene

| Chemical | CAS No. | $AL_{male}$ (μg/day) | $AL_{female}$ (μg/day) |
|---|---|---|---|
| Dicumyl peroxide | 80-43-3 | 2,240 | 1,860 |
| Acetophenone | 98-86-2 | 11,800 | 9,810 |
| Cumyl alcohol | 536-60-7 | 1,800 | 1,800 |
| Alpha methyl styrene | 98-83-9 | 484 | 400 |
| 2,4-Diphenyl-4-methyl-1-pentene | 6362-80-7 | 280 | 232 |

It is to be understood that the description, specific examples and data, while indicating exemplary embodiments, are given by way of illustration and are not intended to limit the present inventions. Various changes and modifications within the present inventions, including combining embodiments in whole and in part, will become apparent to the skilled artisan from the discussion, disclosure and data contained herein, and thus are considered part of the inventions.

What is claimed:

1. A peroxide cross-linked and high temperature melted polymeric material fabricated from peroxide crosslinked ultra-high molecular weight polyethylene containing vitamin-E, wherein ultra-high molecular weight polyethylene is first blended with di-cumyl peroxide and vitamin E to form a blend, wherein said blend is compression molded to obtain a crosslinked and consolidated article and cooled to about room temperature, wherein the crosslinked and consolidated article is then subjected to a high temperature melting (HTM) cycle in a reduced oxygen environment to produce a peroxide cross-linked and high temperature melted polymeric material, wherein the peroxide cross-linked and high temperature melted polymeric material has an acetophenone (ACP) index less than 0.03 and an elongation at break (EAB) less than 400%,
   wherein the high temperature melting cycle comprises
   heating the crosslinked and consolidated article above
      250° C. for at least 50 hours and less than 70 hours,
      wherein during the heating the crosslinked and consolidated article is heated at 295±5° C. for a duration
      that is not longer than 9 hours.

2. The peroxide cross-linked and high temperature melted polymeric material of claim 1, wherein the peroxide cross-linked and high temperature melted polymeric material is fabricated into an insert and the insert is further machined into a medical implant.

3. The medical implant of claim 2 is cleaned, packaged, and gamma sterilized.

4. The peroxide cross-linked and high temperature melted polymeric material of claim 1, wherein the HTM cycle comprises steps of:
heating said crosslinked and consolidated article to a target temperature of 275° C. and holding for a target duration of 4 h;
heating said crosslinked and consolidated article to a target temperature of 295° C. and holding for a target duration of 8 h;
cooling said crosslinked and consolidated article to a target temperature of 275° C. and holding for a target duration of 43 h;
cooling said crosslinked and consolidated article to a target temperature of 130° C. and holding for a target duration of 5 h;
cooling said crosslinked and consolidated article to a target temperature of 115° C. and holding for a target duration of 5 h;
cooling said crosslinked and consolidated article to a target temperature of 105° C. and holding for a target duration of 5 h;
cooling said crosslinked and consolidated article to a target temperature of 40° C. and holding for a target duration of 2 h; and
wherein a temperature of any one of the steps can be 5° C. above or below the target temperatures and a holding duration of any one of the steps can be half hour longer or shorter of said target durations.

5. The HTM cycle of claim 1, wherein the heating temperatures and durations depend on the size of the crosslinked and consolidated article.

6. The HTM cycle of claim 4, wherein the heating temperatures and durations depend on the size of the crosslinked and consolidated article.

7. The crosslinked and consolidated article of claim 5, wherein the crosslinked and consolidated article has a height less than 3 inches.

8. The crosslinked and consolidated article of claim 6, wherein the crosslinked and consolidated article has a height less than 3 inches.

9. The peroxide cross-linked and high temperature melted polymeric material of claim 1, wherein the peroxide cross-linked and consolidated article is heated at 295±5° C. for a duration of at least 8 hours.

10. A wear resistant medical implant fabricated from peroxide crosslinked ultra-high molecular weight polyethylene containing vitamin-E, wherein ultra-high molecular weight polyethylene is first blended with di-cumyl peroxide and vitamin E to form a blend, wherein the blend is compression molded to obtain a crosslinked and consolidated preform and cooled to about room temperature, wherein the crosslinked and consolidated preform is subjected to a high temperature melting (HTM) cycle in a reduced oxygen environment to produce a peroxide crosslinked and high temperature melted polymeric preform, wherein the peroxide cross-linked and high temperature melted polymeric preform has an acetophenone (ACP) index less than 0.03 and an elongation at break (EAB) less than 400%, wherein the peroxide cross-linked and high temperature melted polymeric preform is machined into a medical implant,
wherein the high temperature melting cycle comprises heating the crosslinked and consolidated preform above 250° C. for at least 50 hours and less than 70 hours, wherein during the heating the crosslinked and consolidated preform is heated at 295±5° C. for a duration that is not longer than 9 hours.

11. The wear resistant medical implant of claim 10, wherein the HTM cycle comprises steps of:
heating said crosslinked and consolidated preform to a target temperature of 275° C. and holding for a target duration of 4 h;
heating said crosslinked and consolidated preform to a target temperature of 295° C. and holding for a target duration of 8 h;
cooling said crosslinked and consolidated preform to a target temperature of 275° C. and holding for a target duration of 43 h;
cooling said crosslinked and consolidated preform to a target temperature of 130° C. and holding for a target duration of 5 h;
cooling said crosslinked and consolidated preform to a target temperature of 115° C. and holding for a target duration of 5 h;
cooling said crosslinked and consolidated preform to a target temperature of 105° C. and holding for a target duration of 5 h;
cooling said crosslinked and consolidated preform to a target temperature of 40° C. and holding for a target duration of 2 h; and
wherein a temperature of any one of the steps can be 5° C. above or below the target temperatures and a holding duration of any one of the steps can be half hour longer or shorter of said target durations.

12. The HTM cycle of claim 10, wherein the heating temperatures and durations depend on the size of the crosslinked and consolidated preform.

13. The HTM cycle of claim 11, wherein the heating temperatures and durations depend on the size of the crosslinked and consolidated preform.

14. The crosslinked and consolidated preform of claim 12, wherein the crosslinked and consolidated preform has a height less than 3 inches.

15. The crosslinked and consolidated preform of claim 13, wherein the crosslinked and consolidated preform has a height less than 3 inches.

16. The wear resistant medical implant of claim 10, wherein the peroxide crosslinked and consolidated preform is heated at 295±5° C. for a duration of at least 8 hours.

17. The wear resistant medical implant of claim 10, wherein the wear resistant medical implant is cleaned, packaged, and gamma sterilized.

18. The wear resistant medical implant of claim 10, wherein the wear resistant medical implant is a tibial knee insert.

* * * * *